US009540295B2

(12) United States Patent
Bektesevic et al.

(10) Patent No.: US 9,540,295 B2
(45) Date of Patent: Jan. 10, 2017

(54) PROCESS FOR PRODUCING 2-CHLORO-3,3,3-TRIFLUOROPROPENE AND 2,3,3,3-TETRAFLUOROPROPENE

(71) Applicant: HONEYWELL INTERNATIONAL INC., Morristown, NJ (US)

(72) Inventors: Selma Bektesevic, Williamsville, NY (US); Hsueh Sung Tung, Getzville, NY (US); Haiyou Wang, Amherst, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/348,819

(22) PCT Filed: Sep. 29, 2012

(86) PCT No.: PCT/US2012/058150
§ 371 (c)(1),
(2) Date: Mar. 31, 2014

(87) PCT Pub. No.: WO2013/049743
PCT Pub. Date: Apr. 4, 2013

(65) Prior Publication Data
US 2014/0235904 A1    Aug. 21, 2014

Related U.S. Application Data

(60) Provisional application No. 61/541,744, filed on Sep. 30, 2011.

(51) Int. Cl.
*C07C 17/20* (2006.01)
*C07C 17/25* (2006.01)
(Continued)

(52) U.S. Cl.
CPC ............. *C07C 17/21* (2013.01); *C07C 17/087* (2013.01); *C07C 17/206* (2013.01); *C07C 17/25* (2013.01); *C07C 17/20* (2013.01)

(58) Field of Classification Search
CPC ........ C07C 17/25; C07C 17/20; C07C 17/206; C07C 17/087
See application file for complete search history.

(56) References Cited

U.S. PATENT DOCUMENTS

| 2,931,840 A | 4/1960 | Marquis |
| 4,900,874 A | 2/1990 | Ihara et al. |
(Continued)

FOREIGN PATENT DOCUMENTS

| CN | 101597209 A | 12/2009 |
| CN | 102001911 A | 4/2011 |
(Continued)

OTHER PUBLICATIONS

First Office Action and Search Report dated Dec. 12, 2014, issued in Chinese Patent Application No. 201280057962.X (in English and Chinese).

(Continued)

*Primary Examiner* — Jafar Parsa
*Assistant Examiner* — Medhanit Bahta
(74) *Attorney, Agent, or Firm* — Scully Scott Murphy and Presser

(57) ABSTRACT

The present invention relates, in part, to the discovery that high temperatures during the fluorination of 1,1,2,3-tetrachloropropene (HCO-1230xa) to 2-chloro-3,3,3-trifluoropropene (HCFO-1233xf) results in catalyst instability, reduced selectivity of the conversion, and/or the formation of one or more undesirable by-products. By controlling the reaction temperature, it is shown that the catalyst life may be extended and the selectivity of the reaction improved. Such control similarly results in an overall improvement in the (Continued)

production of certain hydrofluoroolefins, particularly 2,3,3,3-tetrafluoropropene (HFO-1234yf).

19 Claims, 1 Drawing Sheet

(51) Int. Cl.
    *C07C 17/087*     (2006.01)
    *C07C 17/21*     (2006.01)

(56) References Cited

U.S. PATENT DOCUMENTS

| | | | |
|---|---|---|---|
| 5,162,594 | A | 11/1992 | Krespan |
| 7,795,480 | B2 | 9/2010 | Merkel et al. |
| 8,058,486 | B2 * | 11/2011 | Merkel et al. ............... 570/155 |
| 8,071,825 | B2 | 12/2011 | Johnson et al. |
| 8,084,653 | B2 * | 12/2011 | Tung et al. .................. 570/123 |
| 8,119,845 | B2 * | 2/2012 | Merkel et al. ............... 570/156 |
| 8,168,340 | B2 * | 5/2012 | Whitehead et al. .......... 429/414 |
| 2007/0197842 | A1 * | 8/2007 | Mukhopadhyay et al. .. 570/155 |
| 2009/0240090 | A1 | 9/2009 | Merkel et al. |
| 2010/0036179 | A1 | 2/2010 | Merkel et al. |
| 2010/0185030 | A1 * | 7/2010 | Elsheikh et al. ............. 570/160 |
| 2011/0087054 | A1 | 4/2011 | Tirtowidjojo et al. |
| 2011/0105807 | A1 * | 5/2011 | Kopkalli et al. ............. 570/155 |
| 2011/0155942 | A1 * | 6/2011 | Pigamo et al. .................. 252/2 |
| 2011/0218369 | A1 | 9/2011 | Elsheikh et al. |

FOREIGN PATENT DOCUMENTS

| | | |
|---|---|---|
| WO | WO 2007079431 A2 * | 7/2007 |
| WO | WO 2009158321 A1 * | 12/2009 |
| WO | WO2011056441 A2 | 5/2011 |
| WO | WO 20111087825 A1 | 7/2011 |

OTHER PUBLICATIONS

International Search Report dated Mar. 7, 2013 issued in PCT/US2012/058150.

Banks, R. E., et al., "Preparation of 2,3,3,3-tetrafluoropropene from trifluoroacetylacetone and sulphur tetrafluoride" Journal of Fluorine Chemistry 82:171-174 (1997).

Supplementary European Search Report issued in Application No. 12 83 6198 mailed Jul. 13, 2015.

* cited by examiner

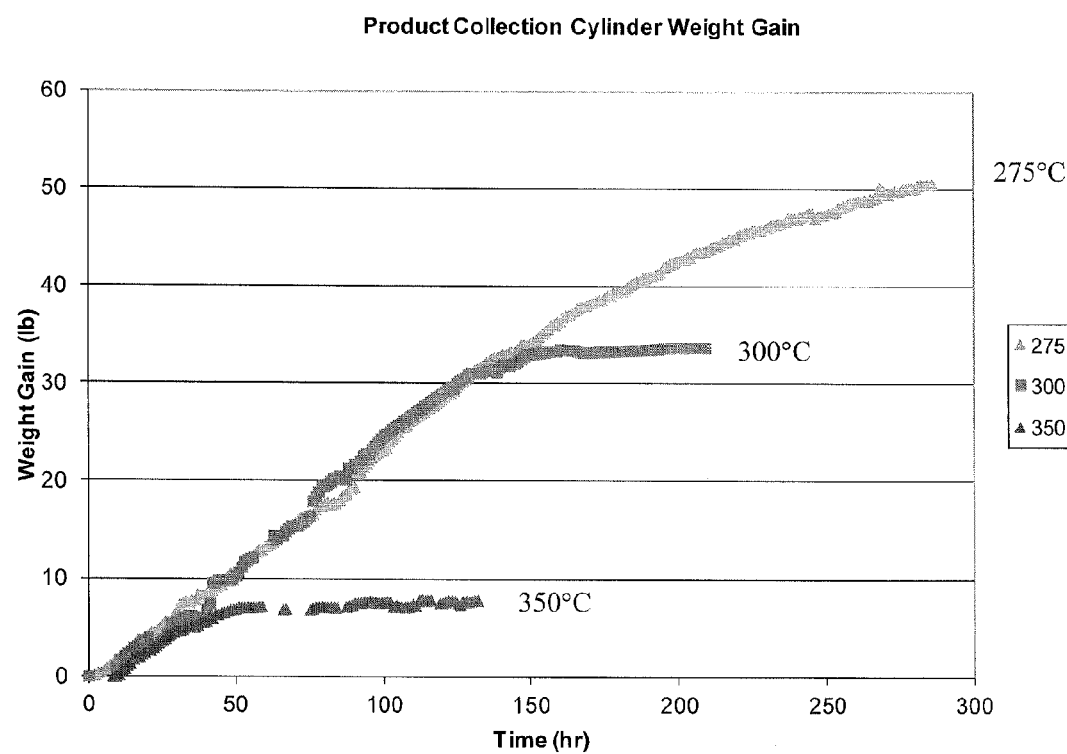

PROCESS FOR PRODUCING 2-CHLORO-3,3,3-TRIFLUOROPROPENE AND 2,3,3,3-TETRAFLUOROPROPENE

CROSS REFERENCE TO RELATED APPLICATIONS

This application claims priority of Provisional Application having Ser. No. 61/541,744, filed on Sep. 30, 2011, the contents of which are incorporated by reference.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Other art showing the formation of fluorinated olefins includes U.S. Pat. Nos. 8,071,825, 8,058,486 and 8,084,653, the contents of all of which are incorporated by reference.

However, there remains a need for an economic means of producing hydrofluoroolefins, such as HFO-1234yf. The present invention satisfies this need among others.

SUMMARY OF INVENTION

The present invention relates, in part, to the surprising discovery that high temperatures during the fluorination of vaporized starting or intermediate feed streams used for the production of HFOs, such as 2,3,3,3-tetrafluoropropene (HFO-1234yf) can result in (a) the instability and deactivation of catalysts used in the process, (b) decreased compound selectivity, and/or (c) an increase in undesirable by-products or impurities. Accordingly, in one aspect, the present invention provides one or more process steps for controlling the reaction temperature so as to prolong the catalyst life and improve the reaction efficiency.

Another aspect of the present invention relates in part to the further discovery that high temperatures and high pressures during the fluorination of vaporized starting or intermediate feed streams used for the production of HFOs, such as 2,3,3,3-tetrafluoropropene (HFO-1234yf) can also result in (a) the instability and deactivation of catalysts used in the process, (b) decreased compound selectivity, and/or (c) an increase in undesirable by-products or impurities.

In one aspect, the present invention relates to a process for preparing 2-chloro-3,3,3-trifluoropropene by providing a starting composition including at least one compound of formula I $$CX_2=CCl-CH_2X \qquad (I)$$

wherein X is independently selected from F, Cl, Br, and I, provided that at least one X is not fluorine and contacting said starting composition with a fluorinating agent to produce a final composition comprising 2-chloro-3,3,3trifluoropropene. In certain embodiments, at least one compound of formula I has at least one chlorine as an X. In further embodiments, at least one compound of formula I has a chlorine at each X position. In even further embodiments, at least one compound of formula I includes 1,1,2,3-tetrachloropropene.

The temperature at which the contacting step occurs is controlled throughout the reaction. In one embodiment, the temperature is controlled such that it does not exceed about 300° C. In further embodiments, the temperature of the contacting step is controlled such that it does not exceed 275° C. or does not exceed 250° C. In further embodiments, the temperature of the reaction remains between about 180 to about 300° C. In even further embodiments, the temperature of the reaction is initiated at a temperature within the range of about 180 to about 200° C. and may be gradually increased by small increments. Such small increments may include, but are not limited to, a temperature increase of about 0.5-20° C., about 1-10° C., about 3-8° C., or about 5° C., as necessary, to maintain the desired product collection rate. In certain embodiments, the product collection rate may be between about 0.1 lbs/hr to about 1.0 lbs/hr per lb of organic feed provided to the reaction, between about 0.3 lbs/hr to about 0.8 lbs/hour per lb of organic feed provided to the reaction, or about 0.5 lbs/hr per lb of organic feed provided to the reaction, wherein the final reaction temperature does not exceed 300° C.

In another aspect of the present invention, the temperature and the pressure at which the contacting step occurs are controlled throughout the reaction. The pressure of the first step may range from about 0 psig to about 150 psig. In one embodiment, the temperature is controlled such that it does not exceed about 300° C. and the pressure is controlled so that the reaction is conducted at a pressure ranging from about 50 psig to about 125 psig. In further embodiments, the temperature of the reaction is controlled such that it does not exceed about 275° C. or does not exceed about 250° C., while, at the same time, maintaining the pressure of the reaction within the range from about 50 psig to about 125 psig. In further embodiments, the temperature of the reaction remains between about 180 to about 300° C. and the pressure ranges from about 50 psig and 125 psig. In even further embodiments, the temperature of the reaction is initiated at a temperature within the range of about 180 to about 200° C. and may be gradually increased by small increments, while having the pressure of the reaction ranging from about 50 psig to about 125 psig. Such small increments of temperature, while the pressure ranges from about 50 psig to 150 psig, may include, but are not limited to, a temperature increase of about 0.5-20° C., about 1-10° C., about 3-8° C., or about 5° C., as necessary, to maintain the desired product collection rate, while maintain the pressure within the aforementioned pressures. In certain embodiments, the product collection rate may be between about 0.1 lbs/hr to about 1.0 lbs/hr per lb of organic feed provided to the reaction, between about 0.3 lbs/hr to about 0.8 lbs/hour per lb of organic feed provided to the reaction, or about 0.5 lbs/hr per lb of organic feed provided to the reaction, wherein the final reaction temperature does not exceed 300° C. and the pressure ranges from about 50 psig to about 125 psig.

The step of contacting the starting composition with a fluorinating agent may occur in the presence of a catalyst. In one aspect, the contacting step occurs in a vapor phase with or without the presence of a vapor phase catalyst. Vapor phase catalysts used for such a reaction include, but are not limited to, a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof. In certain embodiments, the catalyst includes a chromium oxide, such as, but not limited to, $Cr_2O_3$.

In even further aspects, the present invention relates to a process for preparing 2,3,3,3-tetrafluoroprop-1-ene by
  a. providing a starting composition including a compound of formula I $$CX_2=CCl-CH_2X \quad \text{(I)}$$

wherein X is independently selected from F, Cl, Br, and I, provided that at least one X is not fluorine;
  b. contacting the starting composition with a first fluorinating agent to produce a first intermediate composition including 2-chloro-3,3,3-trifluoropropene and a first chlorine-containing byproduct;
  c. contacting the first intermediate composition with a second fluorinating agent to produce a second intermediate composition including 2-chloro-1,1,1,2-tetrafluoropropane; and
  d. dehydrochlorinating at least a portion of the 2-chloro-1,1,1,2-tetrafluoropropane to produce a reaction product including 2,3,3,3-tetrafluoroprop-1-ene.

Again, the temperature of the contacting step (b) may be controlled in accordance with the teachings provided herein.

In another aspect, the temperature and pressure of the contacting step (b) is controlled in accordance with the teachings herein, so that the temperature does not exceed about 300° C. and the pressure ranges from about 50 to about 100 psig.

Additional embodiments and advantages to the present invention will be readily apparent to one of skill in the art, based on the disclosure provided herein.

BRIEF DESCRIPTION OF THE DRAWING

These and other features, aspects, and advantages of the present invention will become better understood with regard to the following description, appended claims, and accompanying drawings.

FIG. 1 depicts graphically the PCC (Product Collection Cylinder) weight gain as a function of time on stream at different reaction temperatures during the reaction of HCO-1230xa to HCFO-1233xf, as described in Example 3.

DETAILED DESCRIPTION OF THE INVENTION

According to one embodiment, the present invention includes a manufacturing process for making 2,3,3,3-tetrafluoroprop-1-ene using a starting material according to formula I:

$$CX_2=CCl-CH_2X \quad \text{(Formula I)}$$

wherein X is independently selected from F, Cl, Br, and I, provided that at least one X is not fluorine. In certain embodiments, the compound(s) of Formula I contains at least one chlorine as an X, a majority of the Xs as chlorine, or all Xs as chlorine. In certain embodiments, the compound(s) of formula I include 1,1,2,3-tetrachloropropene (HCO-1230xa).

The method generally includes at least three reaction steps. In the first step, a starting composition of Formula I (such as 1,1,2,3-tetrachloropropene) is reacted with anhydrous HF in a first vapor phase reactor (fluorination reactor) to produce a mixture of 2-chloro-3,3,3-trifluoropropene (HCFO-1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/$ carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

As provided herein, the temperature of the first step is controlled to extend catalyst life and allow for catalyst regeneration. Controlling the temperature also allows for improved selectivity of the products and reduced impurities or by-products of the reaction. In particular, though not limiting to the invention, one by-product that is substantially reduced by controlling the reaction temperature in accordance with the present invention is vinyl chloride (HCO-1140). It is believed that this compound is a decomposition product of the starting reagent HCO-1230xa. By controlling the reaction temperature, HCO-1230xa decomposition is reduced and the formation of HCO-1140 is minimized or eliminated and selectivity of the conversion process is improved.

The temperature of the first step, particularly fluorination of HCO-1230xa to form HCFO-1233xf, may be controlled before and during the reaction such that the final reaction temperature is prevented from increasing to any point where catalyst life is substantially reduced and/or where selectivity of the product (e.g., HCFO-1233xf) is reduced and/or where the formation of undesirable by-products is observed. In one embodiment, the final temperature does not exceed 300° C., about 275° C., or about 250° C. In an aspect of the present invention, the reaction temperature ranges from a temperature of about 180 to about 300° C. For example, the reaction temperature may be 180° C., 181° C., 182° C., 183° C., 184° C., 185° C., 186° C., 187° C., 188° C., 189° C., 190° C., 191° C., 192° C., 193° C., 194° C., 195° C., 196° C., 197° C., 198° C., 199° C., 200° C., 201° C., 202° C., 203° C., 204° C., 205° C., 206° C., 207° C., 208° C., 209° C., 210° C., 211° C., 212° C., 213° C., 214° C., 215° C., 216° C., 217° C., 218° C., 219° C., 220° C., 221° C., 222° C., 223° C., 224° C., 225° C., 226° C., 227° C., 228° C., 229° C., 230° C., 231° C., 232° C., 233° C., 234° C., 235° C., 236° C., 237° C., 238° C., 239° C., 240° C., 241° C., 242° C., 243° C., 244° C., 245° C., 246° C., 247° C., 248° C., 249° C., 250° C., 251° C., 252° C., 253° C., 254° C., 255° C., 256° C., 257° C., 258° C., 259° C., 260° C., 261° C., 262° C., 263° C., 264° C., 265° C., 266° C., 267° C., 268° C., 269° C., 270° C., 271° C., 272° C., 273° C., 274° C., 275° C., 276° C., 277° C., 278° C., 279° C., 280° C., 281° C., 282° C., 283° C., 284° C., 285° C., 286° C., 287° C., 288° C., 289° C., 290° C., 291° C., 292° C., 293° C., 294° C., 295° C., 296° C., 297° C., 298° C., 299° C., or 300° C. In another embodiment, the reaction is conducted at a pressure ranging from about 50 to about 125 psig and the temperature of the reaction is conducted in the temperature range described herein. In another embodiment, the reaction is conducted at a pressure of about 50 psig, 51 psig, 52 psig, 53 psig, 54 psig, 55 psig, 56 psig, 57 psig, 58 psig, 59 psig, 60 psig, 61 psig, 62 psig, 63 psig, 64 psig, 65 psig, 66 psig, 67 psig, 68 psig, 69 psig, 70 psig, 71 psig, 72 psig, 73 psig, 74 psig, 75 psig, 76 psig, 77 psig, 78 psig, 79 psig, 80 psig, 81 psig, 82 psig, 83 psig, 84 psig, 85 psig, 86 psig, 87 psig, 88 psig, 89 psig, 90 psig, 91 psig, 92 psig, 93 psig, 94 psig, 95 psig, 96 psig, 97 psig, 98 psig, 99 psig, 100 psig, 101 psig, 102 psig, 103 psig, 104 psig, 105 psig, 106 psig, 107 psig, 108 psig, 109 psig, 110 psig, 111 psig, 112 psig, 113 psig, 114 psig, 115 psig, 116 psig, 117 psig, 118 psig, 119 psig, 120 psig, 121 psig, 122 psig, 123 psig, 124 psig, or 125 psig, while maintaining the reaction at the temperature described herein. Alternatively, the reaction may be initiated at a temperature range from about 180° C. to about 200° C. In another embodiment, the reaction may be initiated at a temperature range from about 180° C. to about 200° C., with the pressure being in the range from about 50 psig to about 125 psig. While the reaction may be maintained at one temperature within this temperature range for the duration, it may also be gradually increased in small increments to control the product collection rate. Such small increments may include, but are not limited to, a temperature increase of about 0.5-20° C., about 1-10° C., about 3-8° C., or about 5° C., as necessary, to maintain the desired product collection rate. In certain embodiments, the product collection rate may be between about 0.1 lbs/hr to about 1.0 lbs/hr per lb of organic feed provided to the reaction, between about 0.3 lbs/hr to about 0.8 lbs/hour per lb of organic feed provided to the reaction, or about 0.5 lbs/hr per lb of organic feed provided to the reaction, wherein the final reaction temperature does not exceed 300° C. In addition, the reaction, in one embodiment may be maintained at constant pressure, although the pressure may be fluctuated slightly during the reaction from about 1% to about 2%.

When the compound of formula I is HCO-1230xa, the molar ratio of HF to HCO-1230xa in step 1 of the reaction ranges from about 1:1 to about 1:50 and, in certain embodiments, from about 1:10 to about 1:20. Contact time of the HCO-1230xa with the catalyst may range from about 1 second to about 60 seconds, however, longer or shorter times can be used.

The fluorination reaction is preferably carried out to attain a conversion of about 40% or higher, preferably, about 90% or higher. Conversion is calculated by the number of moles of reactant (HCO-1230xa) consumed divided by number of moles of reactant (HCO-1230xa) fed to the reactor multiplied by 100. The selectivity for HCFO-1233xf attained is preferably about 60% or higher and more preferably about 80% or higher. Selectivity is calculated by number of moles of product (HCFO-1233xf) formed divided by number of moles of reactant consumed.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings, and the like. The vessel is a fixed catalyst bed or fluidized bed. If desired, inert gases such as nitrogen or argon may be employed in the reactor during operation.

In general, the effluent from the fluorination reaction step, including any intermediate effluents that may be present in multi-stage reactor arrangements, may be processed to achieve desired degrees of separation and/or other processing. For example, in embodiments in which the reactor effluent includes HCFO-1233xf, the effluent will generally also include HCl and one or more of HF, 2,3-dichloro-3,3-difluoropropene (HCFO-1232xf), 1,2-dichloro-3,3,3-trifluoropropene (HCFO-1223xd), trichlorofluoropropene (HCFO-1231) isomers, 2-chloro-1,1,1,2-tetrachloropropane (HCFC-244bb), and unreacted HCO-1230xa. Some portion or substantially all of these components of the reaction product may be recovered from the reaction mixture via any separation or purification method known in the art such as neutralization and distillation. It is expected that unreacted HCO-1230xa and HF could be recycled, completely or partially, to improve the overall yield of the desired HCFO-1233xf. HCFO-1232xf and any HCFO-1231 formed may also be recycled.

Optionally, hydrogen chloride is then recovered from the result of the fluorination reaction. Recovering of hydrogen chloride is conducted by conventional distillation where it is removed from the distillate. Alternatively, HCl can be recovered or removed by using water or caustic scrubbers. When a water extractor is used, HCl is removed as an aqueous solution. When caustic scrubbers are used, HCl is just removed from system as a chloride salt in aqueous solution.

In an embodiment, the first fluorination step is conducted in the absence of a stabilizer. Stabilizers are compounds which have been added in halogenation reactions, and in particular halogenation reactions involving alkanes, alkenes, and alkynes, and have been used to prevent the polymerization of the alkanes, alkenes or alkynes under halogenations conditions. Examples of stabilizers include p-tap(4-tert-Amylphenol), methoxy-hydroquinone, 4-methoxyphenol(HQMME), triethylamine, di-isopropyl amine, butylated hydroxy anisole (BHA), thymol or combinations thereof, and the like.

It has been surprisingly been discovered that the catalyst life used in the first fluorination step is shortened dramatically when the temperature of the first step is raised above 300° C. As indicated hereinabove, the catalyst used in the first step of the reaction is a chemical catalyst. It is not a biological catalyst, such as an enzyme, and thus, unlike biological catalysts, its activity would not be expected to be sensitive to a small increase in temperature. However, the present inventors have found that the life of catalysts used in the first fluorination step is indeed affected by temperature. More specifically, it was found that the lifetime of the catalyst is shortened considerably when the first fluorination is conducted at a temperature above about 300° C. This is dramatically seen in FIG. 1 and Example 3 of the present application. When the catalyst is fresh, i.e., has not been used or has been regenerated, regardless of the temperature, the initial rate of the fluorination in the first step of the reaction is approximately the same. However, when the first fluorination reaction is conducted at the higher temperature, the fluorination catalyst is deactivated more quickly than when the reaction is run at the lower temperature. For example, as shown in FIG. 1, at 100 psig, if the first fluorination reaction is conducted at 350° C., after about 50 hours, the fluorination catalyst becomes deactivated. When the first fluorination reaction is conducted at about 300° C. at the same pressure, the catalyst can be used significantly longer before it becomes deactivated. In Example 3, hereinbelow, at 100 psig, it can be used in the first fluorination reaction for about 140 hours before the catalyst becomes deactivated. On the other hand, at the lower temperature at the same pressure, such as 275° C., the fluorination catalyst was still effective in catalyzing the first fluorination reaction, even after being used for 300 hours. Thus, as shown in FIG. 1, a small differential in temperature of 75° C. has quite a dramatic effect in the life of the fluorination catalyst in the first fluorination reaction.

In the second step of the process for forming 2,3,3,3-tetrafluoroprop-1-ene, HCFO-1233xf is converted to 2-chloro-1,1,1,2-tetrafluoropropane (HCFC-244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, the HCFC-244bb is fed to a second vapor phase reactor (dehydrochlorination reactor) to be dehydrochlorinated to make the desired product 2,3,3,3-tetrafluoroprop-1-ene (HFO-1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625, and the like.

Preferred, but non-limiting, catalysts include activated carbon, stainless steel (e.g. SS 316), austenitic nickel-based alloys (e.g. Inconel 625), nickel, fluorinated 10% CsCl/MgO, and 10% CsCl/$MgF_2$, and the like. The reaction temperature ranges from about 300 to about 550° C. and the reaction pressure may range from about 0 to about 150 psig. The reactor effluent may be fed to a caustic scrubber or to a distillation column to remove the by-product of HCl to produce an acid-free organic product which, optionally, may undergo further purification using one or any combination of purification techniques that are known in the art.

The following are examples of the invention and are not to be construed as limiting.

EXAMPLES

Example 1

This example illustrates the continuous vapor phase fluorination reaction of 1,1,2,3-tetrachloropropene (HCO-1230xa) to 2-chloro-3,3,3-trifluoropropene (HCFO-1233xf). The fluorination catalyst for the experiment was fluorinated $Cr_2O_3$.

A continuous vapor phase fluorination reaction system consisting of $N_2$, HF, and organic feed systems, feed vaporizer, superheater, 2 inch ID Monel reactor, acid scrubber, drier, and product collection system was used to study the reaction. The reactor was loaded with 1.8 liters of catalyst. The reactor was then heated to a temperature of about 180° C. with a $N_2$ purge going over the catalyst after the reactor had been installed in a constant temperature sand bath. HF feed was introduced to the reactor (via the vaporizer and superheater) as a co-feed with the $N_2$ for 15 minutes when the $N_2$ flow was stopped. The HF flow rate was adjusted to 1.9 lb/hr and then 1,1,2;3-tetrachloropropene (HCO-1230xa) feed was started to the reactor (via the vaporizer and superheater). The HCO-1230xa feed contained 5 ppm of di-isopropyl amine. The feed rate of HCO-1230xa was kept steady at 1.0 lb/hr and HF feed was kept steady at 1.9 lb/hr for about a 17 to 1 mole ratio of HF to HCO-1230xa. Once the reaction started the catalyst bed temperature rose to about 200° C. The reaction temperature was gradually increased as catalyst deactivation occurred to maintain desired product collection rate, and reaction was stopped once the reaction temperature reached 350° C. The reaction pressure was kept constant at 100 psig during the entire course of reaction. The reaction was continuously run for about 400 hours and 146 lb of HCFO-1233xf and HCFO-1232xf was produced. The average conversion of HCO-1230xa and the average selectivity to HCFO-1233xf were 76.1%, and 84.6%, respectively. The selectivity to unidentified components (compounds other than HCFC-244bb, HCFO-1233xf, HCFO-1232xf, and HCO-1230xa) increased after reaction temperature was raised above 320° C. Initially, sum of GC area % of unidentified components was ~1.5 but increased to above 5% once temperature was increased beyond 320° C. GC-MS analysis revealed that one of the unidentified peaks observed at higher temperatures was due to HCO-1140.

Example 2

All were the same as in Example 1 except that temperature was not raised above 300° C. and pressure was 70 psig in Example 2. The reaction was started at 200° C. As the catalyst was deactivating, temperature was increased in 5° C. increments up to 300° C. Table 1 shows conversion, selectivity to HCFO-1233xf, and selectivity to compounds other than HCFC-244bb, HCFO-1233xf, and HCFO-1232xf as a function of temperature. In general, as catalyst deactivates the selectivity to HCFO-1233xf drops accordingly. As shown in Table 1, increasing temperature beyond 250° C. helps maintain the selectivity to 1233xf high. Selectivity to others is low at reaction temperature<275° C. but it notably increases at reaction temperature>275° C. The deactivation rate is significantly higher for temperatures>250° C. than for temperatures<250° C. The reaction was continuously run for about 1378 hours and 693 lb of HCFO-1233xf and HCFO-1232xf was produced. The average conversion of HCO-1230xa and the average selectivity to HCFO-1233xf were 90.3%, and 87.1%, respectively.

TABLE 1

Conversion, selectivity to HCFO-1233xf, selectivity to others and deactivation rates.

| Time (hr) | Temperature (° C.) | Conversion (%) | Selectivity to HCFO-1233xf (%) | Selectivity to others (%) | Deactivation rate (%/hr) |
|---|---|---|---|---|---|
| 0-400 | 200 | 99.9 | 93 | 0.7 | −0.0022 |
| 737-1114 | 215-250 | 84.0 | 84.7 | 0.4 | −0.0064 |
| 1114-1266 | 250-275 | 66.2 | 87.7 | 0.4 | −0.1264 |
| 1266-1378 | 275-305 | 46 | 91.7 | 1.5 | −0.2417 |

Example 3

This example illustrates the temperature effect in continuous vapor phase fluorination reaction of 1,1,2,3-tetrachloropropene (HCO-1230xa) to 2-chloro-3,3,3-trifluoropropene (HCFO-1233xf). The experiments included in this example were carried out at temperatures higher than 250° C. in the same reactor system as described in Examples 1 and 2. Another batch of fluorinated $Cr_2O_3$ catalyst was used.

Different from Examples 1 and 2, the reaction temperature was fixed at pre-set point and the reaction was run until catalyst lost its activity. The catalyst was then regenerated and the reaction was re-started at a new temperature. Three different temperatures, namely, 275, 300, and 350° C., were studied. Reactor pressure was 100 psig and flow rates of HF and HCO-1230xa were 1.7 and 0.5 lb/hr. respectively. The HCO-1230xa feed contained no di-isopropyl amine. FIG. 1 shows weight gain in PCC (Product Collection Cylinder) as a function of time at three different temperatures. The slope of weight gain vs. time curve was initially the same, suggesting that the conversion of HCO-1230xa was near complete initially. The slope then gradually decreased as catalyst deactivated and eventually flattened as catalyst lost its activity completely. The time to reach the complete loss of catalyst activity was shorter at a higher reaction temperature. For instance, it took about 50 hours at 350° C. versus about 280 hours at 275° C. These results indicate the catalyst lifetime is the shortest at the highest reaction temperature.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A process for preparing 2-chloro-3,3,3-trifluoropropene comprising:
providing a starting composition comprising at least one compound of formula I $$CX_2=CCl-CH_2X \qquad (I)$$

wherein each X is independently F, Cl, Br, or I, provided that at least one X is not fluorine;

contacting said starting composition with a fluorinating agent in the presence of a fluorinating catalyst to produce a final composition comprising 2-chloro-3,3,3-trifluoropropene; and conducting the contacting step at a temperature ranging from about 180° C. to about 300° C. in the presence of said fluorinating catalyst, controlling the temperature of the contacting step such that it does not exceed about 300° C., and when the fluorinating catalyst is deactivating, increasing the temperature of the contacting step in small increments ranging from about 0.5° C. to about 20° C., but not to exceed about 300° C.;

wherein the process is conducted in the vapor phase.

2. The process of claim 1, wherein the temperature of the reaction does not exceed 275° C.

3. The process of claim 1, wherein the temperature of the reaction ranges from about 180° C. to about 300° C.

4. The process of claim 1, wherein the small increments range from about 1° C. to about 10° C.

5. The process according to claim 1 wherein the small increments range from about 3° C. to about 8° C.

6. The process of claim 1, wherein the product collection rate ranges from about 0.1 lbs/hr to about 1.0 lbs/hr per lb of organic feed provided to the reaction.

7. The process according to claim 6 wherein the product collection rate ranges from about 0.3 lbs/hour to about 0.8 lbs/hour of organic feed provided to the reaction.

8. The process of claim 1, wherein at least one compound of formula I is a compound comprising at least one X is a chlorine.

9. The process of claim 1, wherein at least one compound of formula I is a compound where all Xs are chlorine.

10. The process of claim 1, wherein the at least one compound of formula I is 1,1,2,3-tetrachloropropene.

11. The process of claim 1, wherein the fluorination catalyst is selected from the group consisting of a chromium oxide, a chromium hydroxide, a chromium halide, a chromium oxyhalide, an aluminum oxide, an aluminum hydroxide, an aluminum halide, an aluminum oxyhalide, a cobalt oxide, a cobalt hydroxide, a cobalt halide, a cobalt oxyhalide, a manganese oxide, a manganese hydroxide, a manganese halide, a manganese oxyhalide, a nickel oxide, a nickel hydroxide, a nickel halide, a nickel oxyhalide, an iron oxide, an iron hydroxide, an iron halide, an iron oxyhalide, inorganic salts thereof, fluorinated derivatives thereof and combinations thereof.

12. The process of claim 1, wherein the catalyst comprises a chromium oxide.

13. A process for preparing 2,3,3,3-tetrafluoroprop-1-ene comprising:

a. providing a starting composition comprising a compound of formula I $$CX_2=CCl-CH_2X \quad (I)$$ 

wherein each X is independently F, Cl, Br, or I, provided that at least one X is not fluorine;

b. contacting said starting composition with a first fluorinating agent in a vapor phase to produce a first intermediate composition comprising 2-chloro-3,3,3-trifluoropropene in the presence of a fluorination catalyst at a temperature ranging from about 180° C. to about 300° C. and, when the fluorinating catalyst is deactivating, increasing the temperature in small increments ranging from about 0.5° C. about 20° C. and controlling the temperature during the contacting step such that it does not exceed about 300° C.

c. contacting said first intermediate composition with a second fluorinating agent to produce a second intermediate composition comprising 2-chloro-1,1,1,2-tetrafluoropropane; and d. dehydrochlorinating at least a portion of said 2-chloro-1,1,1,2-tetrafluoropropane to produce a reaction product comprising 2,3,3,3-tetrafluoroprop-1-ene.

14. The process of claim 13, wherein the pressure of the reaction ranges from about 50 psig to about 125 psig.

15. The process of claim 13, wherein the temperature during the contacting step (b) does not exceed 275° C.

16. The process of claim 13, wherein the small increments range from about 1° C. to about 10° C.

17. The process according to claim 13 wherein the small increments range from about 3° C. to about 8° C.

18. The process of claim 13, wherein the product collection rate ranges from about 0.1 lbs/hr to about 1.0 lbs/hr per lb of organic feed provided to the reaction.

19. The process according to claim 18 wherein the product collection rate ranges from about 0.3 lbs/hour to about 0.8 lbs/hour of organic feed provided to the reaction.

* * * * *